United States Patent [19]

Diamond et al.

[11] 4,190,595
[45] Feb. 26, 1980

[54] PROCESS FOR DEHALOGENATING THE METAL-HALIDE BOND IN A LOW VALENT GROUP VIII METAL HALIDE COMPLEX

[75] Inventors: Steven E. Diamond, Randolph; Frank Mares, Whippany, both of N.J.

[73] Assignee: Allied Chemical Corporation, Morris Township, Morris County, N.J.

[21] Appl. No.: 931,653

[22] Filed: Aug. 8, 1978

[51] Int. Cl.² .............................................. C07F 15/00
[52] U.S. Cl. ................................ 260/429 R; 260/440; 260/446
[58] Field of Search .................... 260/429 R, 440, 446

[56] References Cited

U.S. PATENT DOCUMENTS

| | | | |
|---|---|---|---|
| 3,547,964 | 12/1970 | Olivier | 260/429 R |
| 3,808,246 | 4/1974 | Fahey | 260/429 R X |
| 3,859,359 | 1/1975 | Keblys | 260/429 R X |
| 3,939,188 | 2/1976 | McVicker | 260/429 R |
| 4,098,807 | 7/1978 | Stone et al. | 260/429 R X |

Primary Examiner—Helen M. S. Sneed
Attorney, Agent, or Firm—Robert J. North; Robert A. Harman

[57] ABSTRACT

A novel process is described for preparing low valent Group VIII metal hydrides, useful as catalysts in the hydrogenation of a large variety of organic compounds, in which a low valent Group VIII metal halide complex, such as $(Ph_3P)_3RhCl$, is reacted with an alkali or alkaline earth metal alkylamide, such as $LiN(CH_3)_2$, containing at least one alkyl group having an alkyl hydrogen atom in the beta position with respect to the metal atom. The metal alkylamide functions both as a dehalogenating and hydrogenating agent in the process. The process can be conducted at room temperature in a suitable organic solvent under an inert atmosphere utilizing the metal alkylamide in stoichiometric quantities. The process is also useful in preparing zero valent Group VIII metal complexes, such as $(Ph_3P)_4Pd°$.

19 Claims, No Drawings

PROCESS FOR DEHALOGENATING THE METAL-HALIDE BOND IN A LOW VALENT GROUP VIII METAL HALIDE COMPLEX

BACKGROUND OF THE INVENTION

1. Field of the Invention

This invention relates to a novel process for producing low valent Group VIII metal hydrides in which a low valent Group VIII metal halide complex is reacted with an alkali or alkaline earth metal alkylamide, containing at least one alkyl group having a hydrogen atom in beta position with respect to the metal atom.

2. Description of the Prior Art

Low valent Group VIII transition metal hydride catalysts are well known in the art as being useful in a wide variety of homogeneously catalyzed hydrogenation processes. For example, hydridotris(triphenylphosphine)rhodium(I), $(Ph_3P)_3RhH$, is a well known catalyst in the homogeneous hydrogenation of olefins. Other processes in which the above catalysts as a class are known to be useful are the homogeneous hydrogenation of ketones, oximes, nitriles and activated esters, as well as in the isomerization, dimerization and oligomerization of olefins.

By the term "low valent Group VIII metals," as used herein, is meant that the metal atom in the Group VIII metal halide complex as well as the resulting metal hydride, containing iron, ruthenium or osmium is in the +2 valence state. For cobalt, rhodium and iridium metal halide complexes and resulting metal hydrides, the metal atom is in the +1 valence state. However, metal atoms of nickel, palladium and platinum are in the +2 valence state in the metal halide complex, but due to the instability of the resulting metal hydride, the resulting metal atom is transformed into the (O) valence state. However, in some cases the metal hydride may be stable.

The symbol "Ph" as used herein, designates the phenyl radical.

Methods of synthesis of low valent Group VIII transition metal hydrides include the use of aqueous ethanolic sodium borohydride in treating triphenylphosphine complexes of chlorides or chloro-anions of rhodium, ruthenium, iridium, osmium and platinum as described in *J. Chem. Soc.* (A), pp. 2947–2954 (1970). However, the disadvantages of the process are that inevitably boron halides are formed in the process which coprecipitate with the product methal hydride along with sodium borohydride reducing agent. Thus, the product is normally contaminated with these materials and usually difficult to purify. Also, excess sodium borohydride reducing agent is usually required to insure high yields in the process which adds to the total cost of the process.

The reference *Inorg Chem.*, Volume 7, pp. 546–551 (1968), describes the preparation of hydrido phosphine complexes of ruthenium and rhodium by treating the complex metal chlorides with either hydrazine or aluminum trialkyls. The disadvantages of this process are that hydrazine presents a severe explosion hazard when exposed to heat and in contact with oxidizing materials. Further, aluminum alkyls are extremely toxic and flammable and have to be used with great caution.

The preparation of triphenylphosphine complexes of rhodium(I) hydride are described in *Naturwissenschaften*, Volume 56, pp. 415–416, and pp. 636–637 (1969), involving, for example the synthesis of tris(triphenylphosphine)rhodium(I) hydride by treating the corresponding chloride with potassium hydroxide in ethanol. However, the formed metal hydrides are exposed to a strongly alkaline medium in which decomposition of the formed product and reduction in yields are likely to occur.

The reference *Inorganic Syntheses*, pp. 121–123 describes the synthesis of tetrakis(triphenylphosphine)palladium(O) by treating palladium dichloride with triphenylphosphine and hydrazine. This process again has the disadvantage of requiring hydrazine as the reducing agent and also requires high reaction temperatures of about 140° C.

The reference *J. Chem. Soc.*, 1186 (1957) describes the preparation of palladium(O) complexes by reacting palladium isocyano complexes with triphenylphosphites and triphenylphosphine compounds. However, the disadvantages in these processes is that isocyano complexes are extremely toxic and the reaction doesn't have the general utility of preparing low valent Group VIII metal hydrides.

The references *J. Am. Chem. Soc.*, Volume 95, pp. 3038–3039, (1973) and reference *J. Org. Chem.*, Volume 41, pp. 2742–2746, (1976) describes the use of palladium black and palladium chloride, respectively in synthesizing unsymmetrical secondary and tertiary amines from substituted amines and converting secondary amines to enamines, respectively. Both references describe the possible participation of a beta-elimination process in producing the final amine products. However, the references do not describe the synthesis of useful low valent Group VIII metal hydride complexes which are not amine adducts.

The reference *Chemical Communications*, pp. 1274–1275 (1971) describes the synthesis of molybdenum amine-hydrides in water by reacting a dicyclopentadienyl molybdenum dimethylthiobromide cation with various amines. Excess amine and high temperatures are described as being necessary in the reaction in which it is postulated that a beta-elimination process may be operating, thus producing the cationic amine-hydride complex. However, the reference does not describe the synthesis of neutral low valent Group VIII metal hydrides useful in homogeneous hydrogenation processes which are not amine complexes.

Due to the wide range of utility of low valent Group VIII metal hydride catalysts the art in this field is constantly concerned with improving known methods for their synthesis particularly with respect to discovering new reducing agents which are not highly toxic, potentially explosive and are not required in excess in the synthesis process.

SUMMARY OF THE INVENTION

We have unexpectedly found that alkali or alkaline earth metal alkylamides, containing at least one alkyl group having a hydrogen atom in beta position with respect to the metal atom, said hydrogen atom being sometimes referred to as an "alkyl beta hydrogen atom," are very useful reagents in dehalogenating low valent Group VIII metal hydride complexes to form the corresponding complex metal hydrides. The metal alkylamide reagents as a class are not highly toxic, or potentially explosive in nature and can be used in a stoichiometric amount in the process and are easily and conveniently prepared.

The novelty of the process resides in the fact that the alkali or alkaline earth metal alkylamides are capable of rapidly dehalogenating low valent Group VIII metal halide complexes and then effecting a hydride transfer of the alkyl beta hydrogen atom to the metal atom via a beta-elimination process. The process is applicable for preparing a wide variety of low valent Group VIII metal hydride complexes and zero valent Group VIII metal complexes, which are described herein by the term "metal complex resulting from the dehalogenation." The metal halide complex contains at least one metal halide bond and ligands which are inert under the reaction conditions and tend to stabilize the resulting metal hydride, or zero valent metal complex, such as organophosphorus, organoarsine, organostibine, carbonyl and tertiary amine ligand groups.

In accordance with this invention there is provided a process for dehalogenating the metal-halide bond in a low valent Group VIII metal halide complex comprising the step of contacting the metal halide complex, containing at least one metal-halide bond with an alkali or alkaline earth metal alkylamide, containing at least one alkyl group containing a hydrogen atom in the beta position with respect to the metal atom, in an inert anhydrous organic solvent therefor, at a temperature from about $-80°$ C. to the decomposition temperature of the metal complex resulting from the dehalogenation, under an inert atmosphere and anhydrous conditions, at a pressure from about 0.001 to 10 atmospheres, said metal alkylamide being present in an amount of at least about 1 equivalent per equivalent of metal-halide bond in said metal halide complex desired to be dehalogenated, and said metal halide complex containing ligands capable of stabilizing the metal halide complex and said metal atom capable of forming metal-ligand bonds capable of stabilizing the metal complex resulting from the dehalogenation.

DESCRIPTION OF THE INVENTION AND PREFERRED EMBODIMENTS

The invention process can be conveniently conducted at room temperature, under an inert atmosphere, at atmospheric pressure or under vacuum by contacting a low valent Group VIII metal halide complex with a metal alkylamide, such as $LiN(CH_3)_2$, in an inert anhydrous organic solvent, such as tetrahydrofuran. The reaction occurs rapidly and by suitable choice of solvent, the product precipitates from solution in very pure form and can be conveniently isolated from byproduct salts and imines which generally are soluble in the solvent. Preferred embodiments of the invention are the preparation of triphenylphosphine complexes of rhodium(I) hydrides, ruthenium(I) hydrides and ruthenium(II) mono- and dihydrides as well as palladium(O) metal triphenylphosphine complexes.

The novel invention process is believed to occur by a beta-elimination process which can be approximated by the following equation:

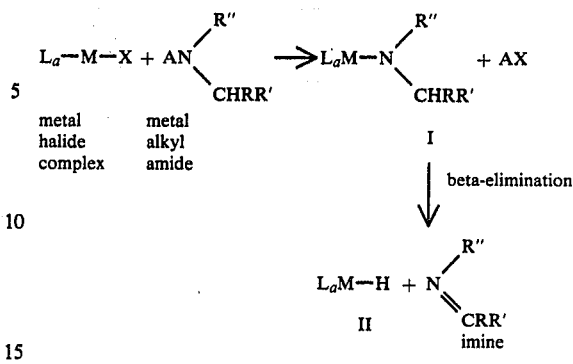

where $L_a$ represents two or more stabilizing ligands, M is a low valent Group VIII metal, X is halogen, A is an alkali or alkaline earth metal cation, R, R' and R'' can be hydrogen or $C_1$–$C_{18}$ linear or branched alkyl. The term "alkyl hydrogen in the beta position" as used herein refers to a methylene hydrogen in a C—H bond. The reaction between the metal halide complex and the metal alkylamide is believed to form an intermediate I, and byproduct alkali metal or alkaline earth metal halide salt. The intermediate I, then is believed to undergo beta elimination of the hydrogen atom and hydride transfer to the metal atom followed by a rearrangement to produce the metal hydride (II) and byproduct imine. Experimental support for this hypothesis is given in Examples 9 and 10. Illustrative of the process is the specific reaction between Wilkinson's reagent, $(Ph_3P)_3RhCl$, and lithium dimethylamide:

wherein hydridotris(triphenylphosphine)rhodium(I) is obtained as well as the imine byproduct.

For low valent Group VIII transition metals having valence of +2, one or two equivalents of the metal alkylamide can be utilized producing either the dihydride or the monohalomonohydride, as illustrated below for tetrakis(triphenylphosphine)ruthenium(II)dichloride:

In the case of the above dihydride, the tetrakis form is relatively more stable as compared to the tris(triphenylphosphine) form.

The above reaction is applicable to the low valent metals in the iron and cobalt triads of Group VIII transition metals including iron, ruthenium and osmium in the iron triad and cobalt, rhodium and iridium in the cobalt triad.

The low valent metals in the nickel triad, nickel, palladium and platinum undergo the same general reaction sequence as illustrated above for the iron and cobalt triads except that the formed metal hydride of the metals ar usually not stable and in such cases undergo an internal redox reaction and rearrangement to produce the complex of the zero valent metal. For example, the reaction of bis(triphenylphosphine)palladium(II) dichloride with lithium dimethylamide is illustrated below.

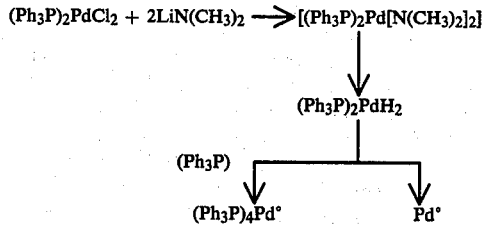

Here, the unstable dihydride complex undergoes rearrangement (per the right hand arrow) to produce palladium zero metal; but, in the presence of stabilizing ligands such as triphenylphosphine (per the left hand arrow) the stable tetrakis(triphenylphosphine)palladium(O) complex is formed.

The novel reagent alkali or alkaline earth metal alkylamide preferably has the formula:

$$ANRR';$$

wherein A is an alkali or alkaline earth metal cation, N is nitrogen, and R and R' being independently selected from hydrogen, deuterium, linear or branched cyclic or acyclic $C_1-C_{18}$ alkyl, said alkyl may also contain substituents inert under the reaction conditions, with the proviso that the metal alkylamide contains at least one alkyl beta hydrogen atom positioned with respect to the metal atom, i.e.,

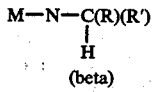
(beta)

Representative examples of alkali and alkaline earth metals, "M" in the above formula, include lithium, sodium, potassium, rubidium, cesium, francium, magnesium, calcium, strontium and barium. A preferred cation is lithium.

Representative examples of R and R' are hydrogen, deuterium, and $C_1-C_{18}$ linear or branched alkyl or $C_6-C_8$ cycloalkyl including methyl, ethyl, n-propyl, isopropyl, n-butyl, isobutyl, secondary butyl, t-butyl, n-pentyl, n-hexyl, n-octyl, n-decyl, n-undecyl, n-dodecyl, n-octadecyl, isooctadecyl, cyclohexyl, methylcyclohexyl and dimethylcyclohexyl. Preferred R and R' groups are methyl, and particularly preferred is where both R and R' are identical and are methyl.

Representative examples of metal alkylamides include lithium dimethylamide, lithium methyl hydrogen amide, lithium diethylamide, lithium hydrogen isopropylamide, sodium dimethylamide, sodium diethylamide, potassium dimethylamide, rubidium dimethylamide, cesium dimethylamide and the bis(dimethylamides) of Be, Mg, Ca, Sr and Ba. A preferred amide is lithium dimethylamide due to its commercial availability, and ease of solubility in the solvents utilized in the process.

The alkali or alkaline earth metal amides can be prepared by known methods in the art and it is usually convenient, from a standpoint of insuring high purity and an anhydrous conditions of the reagent to prepare the reagent immediately prior to the reaction process. For example, the lithium alkylamides can be prepared by action of butyllithium in an appropriate anhydrous solvent such as hexane, with an appropriate amine, such as dimethyl amine, under an inert atmosphere at room temperature. After a brief period of stirring, the solvent and byproduct butane are removed by distillation under reduced pressure, and the final lithium alkylamide reagent is ready for use in the process. Details of the actual preparation of various metal alkylamides are given in Example 1. The direct reaction of an alkali or alkaline earth metal with an amine can also be used to prepare the metal alkylamide.

The amount of metal alkylamide generally utilized in the process is a stoichiometric amount, although less or more can be used. Normally, at least about one equivalent of metal aklylamide per equivalent of metal-halide bond in said metal halide complex desired to be dehalogenated is used.

The low valent Group VIII metal halide complex in the reaction contains a low valent Group VIII metal, as defined hereinabove, at least one metal-halide bond to be dehalogenated and ligands which stabilize the metal halide complex. The Group VIII metal atom is capable of forming metal-ligand bonds capable of stabilizing the metal complex resulting from the dehalogenation. The number of low valent Group VIII metal halide complexes applicable in the instant invention are many, with the proviso that they meet the criteria listed above and include those of the general formula:

$$L_aL'_bL''_cL'''_dMX_eX'_f$$

wherein $L_a$, $L'_b$, $L''_c$, $L'''_d$ are ligands independently selected from the group consisting of carbonyl; organophosphorus ligands of the formula: (QQ'Q"P), wherein Q, Q', Q" are independently selected from linear or branched $C_1-C_{18}$ alkyl, phenyl, or substituted phenyl, said substituents being inert under the reaction conditions; organophosphite ligands of the formula (QO, Q'O, Q"O-P) wherein Q, Q' and Q" are described above; organoarsine ligands of the formula (QQ'Q"As), wherein Q, Q' and Q" are described above; organostibine ligands of the formula: (QQ'Q"Sb), wherein Q, Q' and Q" are described above; tertiary amine ligands containing one to four nitrogen atoms and three to ten carbon atoms; wherein a, b, c, d are integer values of zero or one and the sum of the values of a, b, c and d being two to four; M is a low valent Group VIII metal, described hereinabove; and X and X' are independently selected from hydrogen, deuterium, fluoride, chloride, bromide or iodide, wherein e and f are integer values of zero or one, and the sum of the values of e and f being one or two, with the proviso that at least one X is halogen.

Representative examples of organophosphorous ligands include, those wherein Q, Q' and Q" are independently methyl, ethyl, n-propyl, isopropyl, n-butyl, isobutyl, secondary butyl, t-butyl, n-pentyl, n-hexyl, n-octyl, n-decyl, n-undecyl, n-dodecyl, n-octadecyl, isooctadecyl, phenyl, substituted phenyl including 4-methylphenyl, 2-methylphenyl, 4-methoxyphenyl and 2-methoxyphenyl. Preferred organophosphorus ligand is triphenylphosphine.

Representative examples of specific metal halide complexes containing organophosphorus ligands applicable in the invention include $(Ph_3P)_3RhCl$, $(Ph_3P)_3RhBr$, $(Ph_3P)_3Ru(H)(Cl)$, $(Ph_3P)_3RuCl_2$, $(Ph_3P)_4RuCl_2$, $(Ph_3P)_2PdCl_2$, $(Ph_3P)_3CoCl$, $(Ph_3P)_2(CO)RhCl$, $(Et_3P)_3RhCl$, $(Ph_3P)_2(CO)_2RuCl_2$, $(Ph_3P)_2(CO)IrCl$, $(Ph_3P)_2(CO)IrBr$, $(Ph_3P)_2(CO)IrI$, $(Et_3P)_2NiCl_2$, $(Ph_3P)_3OsCl_2$, $(Ph_3P)_3(CO)OsHBr$, and $(Ph_3P)_2PtCl_2$.

Preferred organophosphorus low valent Group VIII metal halide complexes in the invention are those containing Q, Q' and Q'' as described above and are $(Ph_3P)_3RhCl$, $(Ph_3P)_3Ru(H)(Cl)$, $(Ph_3P)_3RuCl_2$, $(Ph_3P)_4RuCl_2$ and $(Ph_3P)_2PdCl_2$.

Representative examples of organophosphite ligands are the same as described above for organophosphorous ligands except that an oxygen atom is inserted between each Q radical and the phosphorus atom. Specific examples of organophosphite Group VIII metal halide complexes include $[(PhO)_3P]_3RhCl$, $[(PhO)_3P]_2(CO)IrCl$, and those of the formula: $[(RO)_3P]_3RhX$, where $X=Cl$, Br and I and R is $p-ClC_6H_4$, $p-CH_3C_6H_4$ or $m-CH_3C_6H_4$.

Representative examples of organoarsine ligands are the same as described above for organophosphorous ligands except that an arsenic atom replaces the phosphorous atom in the ligand. Specific examples of organoarsine Group VIII metal halide complexes are $(Ph_3As)_3CoCl$, $(Ph_3As)_2(CO)RhCl$, $[(n-propyl)_3As]_3RhCl$, $(Ph_3As)_3RhCl$, $(Et_3As)_2(CO)RhCl$, $(Me_2PhAs)_2(CO)RhCl$, $(PhMe_2As)_4RuBr_2$, $(Ph_3As)_3IrCl$ and $(Ph_3As)_3OsCl_2$.

Representative examples of organostibine ligands are the same as described above for organophosphorus ligands except that an antimony atom replaces the phosphorus atom in the ligand, specific examples of Group VIII metal halide complexes containing organostibine ligands are: $(Ph_3Sb)_3RhCl$, $(Ph_3Sb)_3RhBr$, $(Ph_3Sb)_3RhI$, $(Ph_3Sb)_2(CO)IrBr$, $(Ph_3Sb)_3RuCl_2$ and $(Ph_3Sb)_4OsBr_2$.

Representative examples of tertiary amine ligands are trimethylamine, triethylamine, N,N,N',N'-tetramethylethylenediamine, dipyridyl, terpyridyl, o-phenanthroline and pyridine.

Preferably the sum of the integer values of a, b, c and d is 2–4.

X and X' are preferably hydrogen or chlorine, at least one X being chlorine.

The process can be conducted in the presence of additional ligands to stabilize the resulting metal hydride if it is unstable with respect to the original number or type of ligands present in the metal hydride complex. For example, the bis(triphenylphosphine)palladium(O) complex is unstable, but its formation in the presence of additional triphenylphosphine forms the stable tetrakis(triphenylphosphine)palladium(O) complex. All of the ligands described hereinabove can be correspondingly used in like manner.

By the term "metal complex resulting from the dehalogenation" is meant the low valent Group VIII metal complex monohalo-monohydrides, preferably wherein the metal atom is in a valent state of at least about +1, including +2, and (O) valent metal complexes. Representative examples of metal complex products from the process include: $(Ph_3P)_4RhH$, $(Ph_3P)_3RhH$, $(Ph_3P)_4RuH_2$, $(Ph_3P)_3Ru(H)(Cl)$ and $(Ph_3P)_4Pd^\circ$.

The solvent applicable in the invention process must be a suitable solvent for both the low valent Group VIII metal halide complex and alkali or alkaline earth metal alkylamide, capable of dissolving sufficient material to initiate and maintain the reaction process. The solvent must be inert toward the metal halide complex and metal alkylamide, so as not to chemically alter the structure of either. However, the solvent can participate in a chelating manner with the lithium cation of the metal alkylamide. Suitable solvents for the invention process include: $C_6–C_{12}$ aromatic hydrocarbons, $C_4–C_6$ saturated paraffinic cyclic mono-or diethers, and $C_2–C_6$ saturated paraffinic linear mono-or diethers. Preferred classes of solvents in the process are the aromatic hydrocarbons and ethers described above. Representative examples of specific solvents include toluene, benzene, tetrahydrofuran, dioxane, diethylether, 1,2-dimethoxyethane, or mixtures thereof. Preferred solvents in the reaction process are tetrahydrofuran and p-dioxane.

The amount of solvent used is that sufficient to dissolve a metal halide complex and metal alkylamide sufficiently to initiate and maintain the reaction and to provide a stirrable mixture and is usually about 5 to 10 parts per part of Group VIII metal halide complex, although not limited thereto, larger or smaller amounts also being applicable.

The temperature of the process can be conducted in the range from about $-80^\circ$ C. up to about the decomposition temperature of the resulting dehalogenated product, being about $50^\circ$ to $+200^\circ$ C. The process is preferably conducted at $0^\circ$ to $50^\circ$ C., and more preferably at about $20^\circ–30^\circ$ C., being room temperature.

The process is conducted under an inert atmosphere substantially in the absence of elemental oxygen, which will attack the formed dehalogenated product, and water, which will hydrolyze the alkali or alkaline earth metal alkylamide. The composition of the inert atmosphere can be nitrogen, argon or the like, or mixtures thereof. Preferably the inert atmosphere consists substantially of argon.

The process can be conducted at a pressure from about 0.0001 to 10 atmospheres, under an inert atmosphere or under a vacuum and preferably the process is carried out at one atmosphere of argon.

Yields of metal complex in the reaction process are usually about 60 to 100 percent of theory based on starting Group VIII metal halide complex.

The process can be very advantageously carried out by first preparing the metal alkylamide, as described herein, if commercially unavailable, dissolving the alkylamide in anhydrous tetrahydrofuran or p-dioxane solvent, at room temperature, and atmospheric pressure under an inert atmosphere of argon, adding the low valent Group VIII metal halide complex, preferably a chloride complex, and allowing the resulting solution to stir for about 1 to 15 hours. The resulting dehalogenated metal complex, being either a metal-hydride or zero-valent metal complex, generally precipitates from the tetrahydrofuran solution upon formation, leaving all byproducts and starting materials in the tetrahydrofuran solution.

The product is then filtered, washed with a suitable solvent and dried and is usually ready for use in homogeneously catalysed hydrogenation reactions as is.

Further purification of the product can be affected by standard procedures such as recrystallization.

Apparatus for conducting the process is usually standard glassware inside of a drybox, or synthesis under vacuum in an evacuated vacuum line apparatus, or in a glovebag under an argon atmosphere. The apparatus is conventional and well known to one skilled in the art and will be obvious to one from a reading of this disclosure as to what apparatus to use to carry out the invention process.

Preferred embodiments of the invention and process include:

(A) Wherein the solvent is p-dioxane or tetrahydrofuran, the temperature is about 25° C., the metal alkylamide is lithium dimethylamide, the contacting step is conducted under an atmosphere of argon, the low valent Group VIII metal halide complex is $(Ph_3P)_3RhCl$ and the resulting metal complex is $(Ph_3P)_3RhH$;

(B) As (A) above except that triphenylphosphine is added during the contacting step and the resulting metal complex is $(Ph_3P)_4RhH$;

(C) As (A) above except that one mole of $(Ph_3P)_4RuCl_2$ is reacted with two equivalents of lithium dimethylamide and the resulting metal complex is $(Ph_3P)_4RuH_2$;

(D) As (C) above except that one equivalent of lithium dimethylamide is used and the resulting metal complex is $(Ph_3P)_3Ru(H)(Cl)$;

(E) As (A) above, except that one mole of $(Ph_3P)_2PdCl_2$ is contacted with two equivalents of lithium dimethylamide in the presence of excess triphenylphosphine and the resulting metal complex is $(Ph_3P)_4Pd(O)$.

The following examples are illustrative of the best mode of carrying out the invention process as contemplated by us and should not be construed as being limitations on the scope and spirit of the instant invention.

EXAMPLE 1

General Procedure for Preparation of Lithium Alkyl Amides 2.4 Molar butyllithium in hexane was added to a pressure reactor via syringe under an inert atmosphere of argon. A stoichiometric amount of the appropriate amine as listed below was transferred into the reaction mixture on a vacuum line at liquid nitrogen temperatures. On warming the resulting contents, a white solid began to form. After stirring for thirty minutes, the solvent was removed by distillation under reduced pressure and the resulting lithium alkylamide dried for several hours under vacuum. Microanalytical data for these amide complexes are shown below in Table I.

Table I

| Amide | C Actual | C Theoretical | H Actual | H Theoretical | N Actual | N Theoretical |
|---|---|---|---|---|---|---|
| $LiN(CH_3)_2$ | 46.8 | 47.1 | 11.8 | 11.8 | 27.8 | 27.5 |
| $LiNHCH(CH_3)_2$ | 55.4 | 55.4 | 12.1 | 12.3 | 21.1 | 21.5 |
| $LiN(CD_3)_2$ | 42.1 | 42.1 | 21.8* | 21.1* | 25.0 | 24.6 |
| $LiN(CH_3)(CD_3)$ | 45.2 | 44.4 | 5.65 | 5.56 | 25.5 | 25.9 |
|  |  |  | 11.3* | 11.1* |  |  |

*Deuterium analysis.

EXAMPLE 2

Preparation of Hydridotetrakis(triphenylphosphine)Rhodium(I)

Tris(triphenylphosphine)rhodium(I) chloride (one gram, 1.08 mmole), triphenylphosphine (340 mg, 1.34 mmole), and $LiN(CH_3)_2$ (55 mg, 1.08 mmole) prepared above, were added to a glass pressure reactor in a dry box at about 25° C., under an atmosphere of argon. The reactor was evacuated on the vacuum line and fifteen ml anhydrous tetrahydrofuran (distilled and dried over lithium aluminum hydride) was transferred into the solid mixture. After slow warming from liquid nitrogen temperatures the formation of a yellow precipitate was evident. Filtration under an inert atmosphere followed by washing with hexane (distilled and dried over lithium aluminum hydride) and vacuum drying produced the hydride complex, $(Ph_3P)_4RhH$ in about 75% yield. The resulting product displayed the characteristic metal-hydride absorption band in the infrared region at 2140 $cm^{-1}$. Analysis: calculated for $C_{72}H_{61}P_4Rh$: C, 75.0; H, 5.30; P, 10.8; Rh, 8.94. Found: C, 75.0; H, 5.50; P, 10.8; Rh, 9.22; N, 0; Cl, 0.

EXAMPLE 3

The procedure of Example 2 was repeated except that added triphenylphosphine was not employed. The resulting product, hydridotris(triphenylphosphine)rhodium(I), $(Ph_3P)_3RhH$, was isolated and obtained in about 65 percent yield. The resulting product displayed the characteristic metal-hydride absorption band in the infrared region at 1900 $cm^{-1}$. Analysis: calculated for $C_{62}H_{62}O_2P_3Rh$, as $C_{54}H_{46}P_3Rh.2C_4H_8O$ (di-tetrahydrofuran adduct) C, 71.9; H, 6.00; P, 8.99; Rh, 9.96;. Found: C, 71.2; H, 5.83; P, 9.16; Rh, 10.12; N, O; Cl, trace.

EXAMPLE 4

Following generally the procedure of Example 2, at room temperature (1 gram, 0.83 mmole) tetrakis(triphenylphosphine)ruthenium (II) dichloride was reacted with (80 mg., 1.57 mmole) representing two equivalents of lithium dimethylamide, prepared as in Example 1. The resulting product, dihydridotetrakis(triphenylphosphine)ruthenium(II), $(Ph_3P)_4RuH_2$, was isolated and obtained in about 60% yield. The resulting product displayed the characteristic metal-hydride absorption band at 2080 $cm^{-1}$.

Analysis: calculated for $C_{72}H_{62}P_4Ru$: C, 75.1; H, 5.39; P, 10.8; Ru, 8.77. Found: C, 74.7; H, 5.62; P, 10.8; Ru, 9.00; N, 0; Cl, trace.

EXAMPLE 5

The product from Example 4 was reacted with an excess of chloroform at room temperature under an inert atmosphere to yield the known hydridotris(triphenylphosphine)ruthenium(II) chloride, $(Ph_3P)_3Ru(H)(Cl)$, which displayed the characteristic metal-hydride absorption band at 2020 $cm^{-1}$.

EXAMPLE 6

The procedure of Example 4 was repeated except that (41 mg., 0.80 mmole) of lithium dimethylamide, representing one equivalent, was employed. The resulting product, hydridotris(triphenylphosphine)rutheni-

EXAMPLE 7

The general procedure of Example 2 was carried out using (1 gram, 1.43 mmole) bis(triphenylphosphine)palladium(II) dichloride, $(Ph_3P)_3Pd(Cl_2)$ and (140 mg., 2.75 mmole) lithium dimethylamide. The resulting product was palladium metal, and confirmed literature reports of *J. Chem. Soc.*, 2537 (1962) and *Transition Metal Chemistry*, Number 1, 111 (1965) that the intermediate dihydride, $(Ph_3P)_2PdH_2$, is unstable.

EXAMPLE 8

The procedure of Example 7 was rerun additionally in the presence of (1 gram, 3.82 mmole) triphenylphosphine. The known complex, tetrakis(triphenylphosphine)palladium(0), $(Ph_3P)_4Pd$, was isolated in about 75% yield.

Analysis: calculated for $C_{72}H_{60}P_4Pd$: C, 74.9; H, 5.20; P, 10.7; Pd, 9.19. Found: C, 75.0; H, 5.50; P, 10.7; Pd 8.72; N, 0; Cl, trace.

EXAMPLE 9

The general procedure of Example 2 was repeated except lithium hexadeuterodimethylamide was used in place of lithium dimethylamide and reacted with tris(triphenylphosphine)rhodium(I) chloride and excess triphenylphosphine. The resulting rhodium hydride product exhibited a shift in the metal-hydride absorption band in the infrared region from 2140 cm$^{-1}$ to 1520 cm$^{-1}$ for the metal-deuteride bond.

EXAMPLE 10

The general procedure of Example 2 under anhydrous conditions, was carried out except that lithium isopropylamide, $LiNHCH(CH_3)_2$, was employed in place of lithium dimethylamide. The reaction product was filtered off, and water was added to the remaining filtrate. Analysis of the filtrate by the combined technique of gas chromotography/mass spectrometry revealed the presence of acetone, confirming the fact that isopropylimine, $HN=CH(CH_3)_2$, had been formed and converted to acetone by hydrolysis.

We claim:

1. A process for dehalogenating the metal-halide bond in a low valent Group VIII metal halide complex comprising the step of reacting the metal halide complex, containing at least one metal-halide bond with an alkali or alkaline earth metal alkylamide, containing at least one alkyl group containing a hydrogen atom in the beta position with respect to the metal atom, in an inert anhydrous organic solvent therefor, at a temperature from about $-80°$ C. to the decomposition temperature of the metal complex resulting from the dehalogenation, under an inert atmosphere and anhydrous conditions, at a pressure from about 0.001 to 10 atmospheres, said metal alkylamide being present in an amount of at least about 1 equivalent per equivalent of metal-halide bond in said metal halide complex desired to be dehalogenated, and said metal halide complex containing ligands capable of stabilizing the metal halide complex and said metal atom capable of forming metal-ligand bonds capable of stabilizing the metal complex resulting from the dehalogenation.

2. The process of claim 1 wherein said metal alkylamide has the formula:

ANRR' wherein A is an alkali or alkaline earth metal cation and R and R' being independently selected from hydrogen, deuterium, linear or branched $C_1$–$C_{18}$ alkyl or $C_6$–$C_8$ cycloalkyl.

3. The process of claim 2 wherein said metal alkyl amide has the empirical formula: $LiN(CH_3)_2$, $LiNHCH_3$, $LiN(CH_2CH_3)_2$ and $LiNHCH(CH_3)_2$.

4. The process of claim 1 wherein said low valent Group VIII metal halide complex is of the formula:

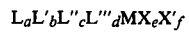

wherein $L_a$, $L'_b$, $L''_c$, $L'''_d$, are ligands independently selected from the group; carbonyl; (QQ'Q''P) wherein Q, Q' and Q'' are independently selected from linear or branched $C_1$–$C_{18}$ alkyl, phenyl, or substituted phenyl, with one or more groups inert under the reaction conditions; (QO, Q'O, Q''O-P) wherein Q, Q' and Q'' being defined as above; (QQ'Q''As), wherein Q, Q' and Q'' being defined as above; (QQ'Q''Sb) wherein Q, Q' and Q'' being defined as above; tertiary amines containing 1 to 4 nitrogen atoms and 3 to 10 carbon atoms; wherein a, b, c and d are integer values of zero or one and the sum of the values of a, b, c and d being two to four; M being a low valent Group III metal; X and X' being independently selected from hydrogen, deuterium, fluoride, chloride, bromide and iodide; e and f being integer values of zero or one and the sum of the values of e and f being one or two, with the proviso that at least one X is halide.

5. The process of claim 4 wherein said metal halide complex has the empirical formula: $(Ph_3P)_3RhCl$, $(Ph_3P)_3RuHCl$, $(Ph_3P)_3RuCl_2$, $(Ph_3P)_4RuCl_2$, or $(Ph_3P)_2PdCl_2$.

6. The process of claim 1 wherein said solvent is a $C_6$–$C_{12}$ aromatic hydrocarbon, $C_4$–$C_6$ saturated paraffinic cyclic mono- or diether, $C_2$–$C_6$ saturated paraffinic linear mono- or diether, or mixtures thereof.

7. The process of claim 6 wherein said solvent is toluene, benzene, tetrahydrofuran, dioxane, diethylether, 1,2-dimethoxyethane, or mixtures thereof.

8. The process of claim 1 wherein the temperature is about 0° to 50° C.

9. The process of claim 1 wherein the process is conducted under a pressure of about one atmosphere.

10. The process of claim 1 wherein said atmosphere consists essentially of argon or nitrogen.

11. The process of claim 1 further comprising adding triphenylphosphine as a stabilizing ligand during the reacting step.

12. The process of claim 1 wherein the metal complex resulting from the dehalogenation is a low valent Group VIII metal hydride complex, containing said metal in a valent state of at least one.

13. The process of claim 1 wherein the metal complex resulting from the dehalogenation is a low valent Group VIII metal complex, containing said metal in a zero valence state.

14. The process of claim 1 wherein the solvent is tetrahydrofuran, the temperature is about 25° C., the metal alkylamide is $LiN(CH_3)_2$, and the reacting step is conducted under an atmosphere consisting essentially of argon.

15. The process of claim 14 wherein the low valent Group VIII metal halide complex is $(Ph_3P)_3RhCl$ and the metal complex resulting from the dehalogenation is (Ph₃P)₃RhH.

16. The process of claim 15 wherein triphenylphosphine is added during the reacting step and the product resulting from the dehalogenation being (Ph₃P)₄RhH.

17. The process of claim 14 wherein the low valent Group VIII metal halide complex is (Ph₃P)₄RuCl₂, one mole of said metal halide being reacted with two equivalents of lithium dimethylamide, and the product resulting from the dehalogenation being (Ph₃P)₄RuH₂.

18. The process of claim 14 wherein the low valent Group VIII metal halide is (Ph₃P)₄RuCl₂, one mole of said metal halide complex being reacted with one equivalent of lithium dimethylamide, and the product resulting from the dehalogenation being (Ph₃P)₃Ru(H)(Cl).

19. The process of claim 14 wherein the low valent Group VIII metal halide complex is (Ph₃P)₂PdCl₂, one mole of said metal halide being reacted with two equivalents of lithium dimethylamide, in the presence of triphenylphosphine, and the product resulting from the dehalogenation being (Ph₃P)₄Pd°.

* * * * *

UNITED STATES PATENT AND TRADEMARK OFFICE
CERTIFICATE OF CORRECTION

PATENT NO. : 4,190,595
DATED : February 26, 1980
INVENTOR(S) : S. E. Diamond and F. Mares It is certified that error appears in the above-identified patent and that said Letters Patent are hereby corrected as shown below:

Col. 1, line 14, "2. Description . . ." should read
--2. Brief Description . . .--.

Col. 1, line 49, "methal" should read --metal--.

Col. 5, line 3, "ar" should read --are--.

Col. 12, line 27, "Group III" should read --Group VIII--.

Signed and Sealed this

Fifteenth Day of July 1980

[SEAL]

Attest:

SIDNEY A. DIAMOND

Attesting Officer

Commissioner of Patents and Trademarks